United States Patent [19]

McKernan et al.

[11] Patent Number: 5,698,521
[45] Date of Patent: Dec. 16, 1997

[54] NATIVE CALCITONIN MIMETICS

[75] Inventors: Patricia A. McKernan, Woodinville; Lennie Chen, Renton; Charles Petrie, Woodinville; James Piggott, Bothell; Robert R. West, Seattle; Shirley Gasper, Carnation, all of Wash.; Colin Lellis, Lansdale, Pa.

[73] Assignee: ZymoGenetics, Inc., Seattle, Wash.

[21] Appl. No.: 416,602

[22] Filed: Apr. 4, 1995

[51] Int. Cl.$^6$ .................... A61K 38/00; C07K 5/00; C07K 7/00
[52] U.S. Cl. .................. 514/13; 530/307; 530/326
[58] Field of Search .................. 514/13; 530/307, 530/326

[56] References Cited

FOREIGN PATENT DOCUMENTS 2218102  11/1989  United Kingdom.
2257908  1/1993  United Kingdom.

OTHER PUBLICATIONS

Yates, et al., *Endocrinology* 126 (6): 2845–2849, 1990.

Orlowski et al., *Eur. J. Biochem.* 162: 399–402, 1987.

Rinehart et al., *J. Am. Chem. Soc.* 103: 6517–6520, 1981.

Moe et al., *Biochemistry* 24: 1971–1976, 1985.

*Primary Examiner*—Avis M. Davenport
*Attorney, Agent, or Firm*—Susan E. Lingenfelter

[57] ABSTRACT

The invention provides isolated, biologically active native calcitonin mimetics and related methods. These small 16 and 17 amino acid proteins mimic the interaction of calcitonin on its receptor, and also exhibit bone resorptive inhibiting activity.

5 Claims, No Drawings

NATIVE CALCITONIN MIMETICS

BACKGROUND OF THE INVENTION

Bone is a dynamic tissue, and homeostasis in the adult skeleton requires a balance between bone resorption and bone formation. Osteoclasts and osteoblasts play a key role in this balance, with osteoclasts initiating bone resorption and osteoblasts synthesizing and depositing new bone matrix. Imbalances in bone homeostasis are associated with such conditions as osteoporosis, Paget's disease, and hyperparathyroidism.

The activities of osteoclasts and osteoblasts are regulated by complex interactions between systemic hormones and the local production of growth factors and cytokines. Calcitonin, a peptide hormone secreted by the thyroid and thymus of mammals, plays an important role in maintaining bone homeostasis. Calcitonin inhibits bone resorption through binding and activation of a specific calcitonin receptor on osteoclasts (*The Calcitonins—Physiology and Pharmacology*, Azria (ed.), Karger, Basel, Su., 1989), with a resultant decrease in the amount of calcium released by bone into the serum. This inhibition of bone resorption has been exploited, for instance, by using calcitonin as a treatment for osteoporosis, a disease characterized by a decrease in the skeletal mass often resulting in debilitating and painful fractures. Calcitonin is used in the treatment of Paget's disease as well, where it also provides rapid relief from bone pain, which is frequently the primary symptom associated with this disease. This analgesic effect has also been demonstrated in patients with osteoporosis, metastatic bone disease, and has been reported to relieve pain associated with diabetic neuropathy, cancer, migraine and post-hysterectomy. Reduction in bone pain occurs before the reduction of bone resorption.

Salmon calcitonin has been shown to be considerably more effective in arresting bone resorption than human forms of calcitonin. There are several hypotheses to explain this observation, which include: 1) salmon calcitonin is more resistant to degradation; 2) salmon calcitonin has a lower metabolic clearance rate (MCR); and 3) salmon calcitonin may have a slightly different conformation, resulting in a higher affinity for bone receptor sites.

Despite the advantages associated with the use of salmon calcitonin in humans, there are also disadvantages. For treatment of osteoporosis, for instance, the average cost can exceed $75 a week and involve daily prophylactic administration for 5 or more years. In the United States, calcitonin must be administered by injection, and since the disease indications for this drug are not usually life threatening, patient compliance can be low. In addition, some patients develop antibodies to non-human calcitonin. Therefore, mimetics of human calcitonin that are potent inhibitors of bone resorption, less expensive for the consumer, more convenient to administer (i.e., orally), and non-immunogenic are needed.

SUMMARY OF THE INVENTION

The present invention provides isolated compounds that are biologically active calcitonin mimetics. As used herein, the term "calcitonin mimetic" refers to any compound with the ability to mimic the interaction of calcitonin on its receptor and, by such interaction, stimulate G-protein-mediated activation of adenyl cyclase. The term "biologically active" is used herein to denote calcitonin mimetics that exhibit bone resorption inhibiting activity.

Within one aspect this invention provides a biologically active calcitonin mimetic selected from the group consisting of 2807 A: Acetyl-Trp-Xaa1-Gln-2-aminoisobutyric acid (Aib)-Ile-Thr-Aib-Leu-Aib-Pro-Gln-Aib-Pro-Aib-Xaa2-Phe-Gly (SEQ ID NO. 1), 2807 B: Acetyl-Trp-Xaa1-Gln-Aib-Ile-Thr-Aib-Leu-Aib-Pro-Gln-Aib-Pro-Aib-Xaa2-Phe (SEQ ID NO. 2), and pharmaceutically acceptable salts thereof; wherein Xaa1 is Isovaline (Iva) and Xaa2 is 4-Methyl proline (MePro).

In another aspect of this invention a pharmaceutical composition is provided that comprises a biologically active calcitonin mimetic as disclosed above and a pharmaceutically acceptable carrier. A third aspect of this invention comprises a composition being orally administered to a patient in need of this synthetic calcitonin mimetic.

This and other aspects of the invention will become evident upon reference to the following detailed description.

DETAILED DESCRIPTION OF THE INVENTION

The calcitonin mimetics of the present invention were originally identified by a high throughput screen of natural product extracts. The calcitonin mimetics 2807 A (SEQ. ID. NO. 1) and B (SEQ. ID. NO. 2) of the present invention are produced by aerobic fermentation of fungal culture ZG 2807, originally isolated from deer excrements collected on a grass meadow in Denmark. The culture was taxonomically characterized as *Acremonium rutilum* W. Gams at Centraalbureau voor Schimmelcultures, Oosterstraat 1, 3742 SK Baarn, The Netherlands.

This fungus is maintained in the Culture and Metabolites Collection of Novo Nordisk A/S, Novo Alle, 2880 Bagsvaerd, Denmark as culture number NN006248/N0043. A viable culture of this microorganism was deposited with the Centraalbureau voor Schimmelcultures, Oosterstraat 1, 3742 SK Vaarn, The Netherlands on Dec. 27, 1994. It has been deposited under the Budapest Treaty and assigned the strain designation CBS 650.94 by such depository.

The calcitonin mimetics described herein are unique and quite different from native calcitonins, which are secreted by the thyroid and thymus glands of mammals and the ultimobranchial glands of lower vertebrates. Known, naturally occurring calcitonins are all 32-amino acid polypeptides having an amidated carboxy terminus and an intramolecular disulfide bond between cysteine residues in the 1 and 7 positions. The claimed calcitonin mimetics are small peptides containing 16 or 17 amino acid residues and have a C-terminal carboxylic group. They share little sequence homology with native calcitonins; threonine at position 6, a polar uncharged hydrophilic amide at position 3, a hydrophobic nonpolar uncharged aliphatic amino acid at position 8 and a hydrophobic nonpolar uncharged amino acid at position 16. Both are helical. The calcitonin mimetics of the present invention contain six α-alkylated α amino acids, five Aib and one Iva, and have one MePro. The calcitonin mimetics disclosed herein are more structurally similar to the peptaibol class of compounds, in particular Zervamicin II-3 (Rhinehart et al., *J. Am. Chem. Soc.* 103:6517–20, 1981).

A variety of modified calcitonins are known in the art, including calcitonins having amino acid substitutions (e.g. U.S. Pat. Nos. 4,824,936; 4,764,589; 4,663,309 and 4,658,014), deletions (e.g. U.S. Pat. Nos. 4,820,804; 4,764,591; 4,639,511; 4,605,514 and 4,537,716), or truncations (Feyen et al., *Biochem. Biophys. Res. Comm.* 187:8–13, 1992); calcitonins containing D-amino acid substitutions (U.S. Pat. No. 4,652,627); calcitonins modified by sugar and formyl residues (UK Patent No. 2,218,102A); and noncyclical calcitonin analogs (Yates et al., *Endrocrinology* 126:2845–49, 1990). All modifications were made directly to the sequences of either native human or salmon calcitonin and bear little homology to the mimetics of the present invention.

Peptides are not a normally expected outcome of the high throughput screening process described herein. The screening strategy made use of organic solvent extracted samples, which conveyed a dual benefit for this screen. Many normal peptides and proteins are more soluble in the aqueous phase and should therefore be eliminated before screening has begun, and the aqueous phase can contain contaminants which have lead to interference in other assay systems. This screening strategy should tend to give compounds that are lipophilic and, with some exceptions, nonpeptidic small molecules.

Since one of the principal functions of the gastrointestinal tract is digestion of proteins and peptides, normal peptides used as oral therapeutic agents face some challenges, which include the possibility of metabolism in both the gut and the intestinal lumen, poor transport across the intestinal mucosa, and rapid first-pass clearance in vivo, which may contribute to overall low bioavailability (Verhoef et al., *Eur. J. Drug Met. Pharmacokin.* 15:83–93, 1990; Aungst, *J. Pharm. Sci.* 82:979–87, 1993). The unique structures of the calcitonin mimetics of this invention have overcome some of these limitations. For example, as described above these mimetics contain alkylated α amino acids distributed throughout the peptide, which can have the effect of reducing susceptibility to in vivo enzymatic breakdown, and contribute to the helical nature of the molecules. The calcitonin mimetics of the current invention are also hydrophobic and sterically hindered; both of these features enhance protease stability and gastrointestinal absorption. Further modifications can be made to the compounds of the present invention by manipulating such characteristics as lipophilicity, hydrophilicity and solubility. Preferred methods would include glycosylation or pegylation at the C-terminus. A particularly preferred method involves activation of the C-terminus with a carbodiimide and reaction of the activated peptide with an amine, such as glucosamine, aminoethylPEG, or other alkyl- or aryl-amines.

The discovery of the present invention is a result of screening large numbers of samples (could include for instance; microbial culture extracts, plant extracts, marine extracts, pure chemical compounds, peptides, and combinatorial libraries) using an assay system that permits rapid identification of substances having selective calcitonin receptor activity on cells expressing the calcitonin receptor. The calcitonin receptor is a member of the G-protein receptor family and transduces signal via activation of adenylate cyclase, leading to elevation of cellular cAMP levels (Lin et al., *Science* 254:1022–24, 1991). This assay system exploits the receptor's ability to elevate cAMP levels as a way to detect other molecules that are able to stimulate the calcitonin receptor and initiate signal transduction.

Receptor activation can be detected by: (1) measurement of adenylate cyclase activity (Salomon et al., *Anal. Biochem.* 58:541–48, 1974; Alvarez and Daniels, *Anal. Biochem.* 187:98–103, 1990); (2) measurement of change in intracellular cAMP levels using conventional radioimmunoassay methods (Steiner et al., *J. Biol. Chem.* 247:1106–13, 1972; Harper and Brooker, *J. Cyc. Nucl. Res.* 1:207–18, 1975); or (3) through use of a cAMP scintillation proximity assay (SPA) method (Amersham Corp., Arlington Heights, Ill.). While these methods provide sensitivity and accuracy, they involve considerable sample processing prior to assay, are time consuming, involve the use of radioisotopes, and would be cumbersome for large scale screening assays.

An alternative assay system involves selection of substances that are able to induce expression of a cyclic AMP response element (CRE)-luciferase reporter gene, as a consequence of elevated cAMP levels, in cells expressing a calcitonin receptor, but not in cells lacking calcitonin receptor expression, as described in pending U.S. patent application Ser. No. 08/100,887, which is incorporated herein in its entirety.

Elucidating the structure of the calcitonin mimetics can be accomplished by conventional methods, well known in the art (*Protein purifications, Methods in Enzymology Vol.* 182: Deutscher, M (ed.), Acad. Press, San Diego, 1990), which may include nuclear magnetic resonance (NMR), mass spectrometry (MS), circular dichroism (CD) and optical rotation, and protein crystallization. Additional characterization can be achieved using size and molecular weight determination, amino acid analysis, N-terminal sequence analysis, and peptide mapping.

The calcitonin mimetics of the present invention can be synthesized by solid phase or solution phase methods conventionally used for the synthesis of peptides (see, for example, Merrifield, R. B., *J. Amer. Chem. Soc.* 85: 2149–54, 1963; Birr, C., *Aspects of the Merrifield Peptide Synthesis*, Springer-Verlag, Heidelberg, 1978; Carpino, L.A., *Acc. Chem. Res.* 6:191–98, 1973; Kent S.B., *Ann. Rev. Biochem.* 57:957–89, 1988; Gregg et al., *Int. J. Peptide protein Res.* 35:161–214, 1990; *The Peptides, Analysis, Synthesis, Biology,* Vols. 1, 2, 3, 5: Gross, E and Meinhofer, J. (eds.), Acad. Press, New York, 1979; and Stewart et al., *Solid Phase peptide Synthesis*, 2nd. ed., Pierce Chem. Co., Rockford, Ill., 1984; which are incorporated herein by reference in their entirety.) The use of solid phase methodology is preferred. Briefly, an N-protected C-terminal amino acid residue is linked to an insoluble support, such as divinylbenzene cross-linked polystyrene, polyacrylamide resin, Kieselguhr/polyamide (pepsyn K), controlled pore glass, cellulose, polypropylene membranes, acrylic acid-coated polyethylene rods or the like. Cycles of deprotection, neutralization (in the case of BOC chemistry, vide infra) and coupling of successive protected amino acid derivatives are used to link the amino acids from the C-terminus according to the amino acid sequence. Preferred solid supports are divinylbenzene cross-linked polystyrene resins, which are commercially available in a variety of functionalized forms, including chloromethyl resin, hydroxymethyl resin, paraacetamidomethyl resin, benzhydrylamine (BHA) resin, 4-methylbenzhydrylamine (MBHA) resin, oxime resins, 4-alkoxybenzyl alcohol resin, 4-(2',4'-dimethoxyphenylaminomethyl)-phenoxymethyl resin, 2,4-dimethoxybenzhydrylamine resin, and 4-(2',4'-dimethoxyphenyl-FMOC-aminomethyl)-phenoxyacetamidonorleucyl-MBHA resin (Rink amide MBHA resin). Acid sensitive resins, such as Sasrin and 2-chlorotrityl, are particularly preferred because they require mild acid cleavage, thus preventing possible cleavage of Aib-Pro bonds. A particularly preferred protecting group for α-amino acids is base-labile 9-fluorenylmethoxycarbonyl (FMOC). Suitable protecting groups for the side chain functionalities of amino acids chemically compatible with BOC (t-butyloxycarbonyl) and FMOC groups are well known in the art. When using FMOC chemistry, the following protected amino acid derivatives are preferred: FMOC-Cys(Trit), FMOC-Ser(But), FMOC-Asn(Trit), FMOC-Leu, FMOC-Thr(Trit), FMOC-Val, FMOC-Gly, FMOC-Lys (Boc), FMOC-Gln(Trit), FMOC-Glu(OBut), FMOC-His (Trit), FMOC-Tyr(But), FMOC-Arg(PMC (2,2,5,7,8-pentamethylchroman-6-sulfonyl)), FMOC-Arg(BOC) 2, and FMOC-Pro. The amino acid residues can be coupled by using a variety of coupling agents and chemistries known in the art, such as direct coupling with DIC (diisopropylcarbodiimide), DCC (dicyclohexylcarbodiimide), BOP (benzotriazolyl-N-oxytrisdimethylaminophos-phonium hexafluorophosphate), PyBOP (benzotriazole-1-yl-oxy-tris-pyrrolidino phosphonium hexafluorophosphate), PyBrOP (bromo-tris-pyrrolidino-phosphonium hexafluorophosphate); via preformed symmetrical anhydrides; via active esters such as pentafluorophenyl esters; or via preformed HOBt (1-hydroxybenzotriazole) active esters or by using FMOC-amino acid fluoride and chlorides or by using FMOC-amino acid-N-carboxy anhydrides. Activation with HBTU ([2-(1H-benzotriazole-1-yl),1,1,3,3-tetramethyluronium hexafluorophosphate]) or HATU ([2-(1H-7-aza-benzotriazole-1-yl),1,1,3,3-tetramethyluronium hexafluorophosphate]) in the presence of HOBt or HOAt (7-azahydroxybenztriazole) is preferred.

The solid phase method can be carried out manually, although automated synthesis on a commercially available peptide synthesizer (e.g., Applied Biosystems 431A or the like) is preferred. In a typical synthesis, the first amino acid (the C-terminal FMOC-Phe) is loaded on the chlorotrityl resin. Successive deprotection (with 20% piperidine/NMP (N-methylpyrrolidone)) and coupling cycles according to ABI FastMoc protocols (ABI user bulletins 32 and 33, Applied Biosystems Inc.) are used to build the whole peptide sequence.

The synthetic calcitonin mimetic peptide is cleaved from the resin and deprotected by treatment with TFA (trifluoroacetic acid) containing appropriate scavengers. Many such cleavage reagents, such as Reagent K (0.75 g crystalline phenol, 0.25 ml ethanedithiol, 0.5 ml thioanisole, 0.5 ml deionized water, 10 ml TFA) and others, can be used. The peptide is separated from the resin by filtration and isolated by ether precipitation. Further purification may be achieved by conventional methods, such as gel filtration and reverse phase HPLC (high performance liquid chromatography).

Calcitonin mimetics according to the present invention can be prepared in the form of pharmaceutically acceptable salts, especially base-addition salts including salts of organic bases and inorganic bases. The base-addition salts of the acidic amino acid residues are prepared by treatment of the peptide with the appropriate base or inorganic base, according to procedures well known to those skilled in the art, or the desired salt may be obtained directly by lyophilization out of the appropriate base.

Assessing the oral bioavailability of the calcitonin mimetics of the present invention can be done by a number of methods well known in the art (Aungust, *J. Pharm. Sci.* 82:979–87, 1993). These include determining stability at acidic pH (pH 2.0, 37° C., 6 hours) and stability to enzymatic breakdown under conditions appropriate for the selected enzyme. Stability to enzymatic breakdown in liver and kidney homogenates can also be measured. Absorption and transport can be determined from several in vitro models known in the art, including everted sacs, brush border membrane vesicles, intestinal rings, and several cell lines of renal (MDCK I, MDCK II and LLC-$PK_1$) or intestinal ($T_{84}$ and Caco-2) origin.

Well established animal models are available to test in vivo efficacy of calcitonin mimetics. For example, the hypocalcemic rat or mouse model can be used to determine the effect on serum calcium, and the ovariectomized rat or mouse can be used as a model system for osteoporosis. Bone changes seen in these models and in humans during the early stages of estrogen deficiency are qualitatively similar. Calcitonin has been shown to be an effective agent for the prevention of bone loss in ovariectomized women and rats (Mazzuoli et al., *Calcif. Tissue Int.* 47:209–14, 1990; Wronski et al., *Endocrinology* 129:2246–50, 1991). High dose estrogen has been shown to inhibit bone resorption and to stimulate bone formation in an ovariectomized mouse model (Bain et al., *J. Bone Miner. Res.* 8:435–42, 1993.

Biologically active calcitonin mimetics of the present invention are therefore contemplated to be advantageous for use in therapeutic applications for which calcitonin is useful. Such applications where calcitonin mimetics of the present invention may be used, for example, are in the treatment of osteoporosis, Paget's disease, hyperparathyroidism, osteomalacia, idiopathic hypercalcemia of infancy and other conditions. The calcitonin mimetics can also be used to inhibit gastric secretion in the treatment of acute pancreatitis and gastrointestinal disorders, and as analgesics, in particular for bone pain.

Calcitonin mimetics of the present invention can be formulated with a pharmaceutically acceptable carrier for parenteral, oral, nasal, rectal, or transdermal administration or the like, according to conventional methods. Formulations may further include one or more diluents, fillers, emulsifiers, preservatives, buffers, excipients, and the like, and may be provided in such forms as liquids, powders, emulsions, suppositories, liposomes, transdermal patches and tablets, for example. One skilled in the art may formulate the compounds of the present invention in an appropriate manner, and in accordance with accepted practices, such as those disclosed in *Remington's pharmaceutical Sciences*, Gennaro (ed.), Mack Publishing Co., Easton, Pa. 1990 (which is incorporated herein by reference in its entirety).

The oral absorption of the calcitonin mimetics can be further enhanced by use of drug permeation enhancers, such as salicylates; surfactants such as bile acids and their salts, polyoxyethylene fatty acids or fatty acyl ethers; chelating agents such as ethylenediamine tetraacetic acid; and solvents such as dimethylsulphoxide and ethanol (Verhoef et al., *Eur. J. Drug Metb. Pharmacokinet.* 5:83–93, 1990).

Pharmaceutical compositions of the present invention are administered at daily to weekly intervals. An "effective amount" of such a pharmaceutical composition is an amount that provides a clinically significant reduction in serum calcium, inhibition of bone resorption, inhibition of gastric secretion, reduction of bone pain or other beneficial effect. Such amounts will depend, in part, on the particular condition to be treated, age, weight, and general health of the patient, and other factors evident to those skilled in the art. Therapeutic doses for the treatment of osteoporosis may range from 50–150 International Units (I.U.). Potency is estimated by comparing the hypocalcemic effect in rats with that of a standard preparation and is expressed in International Units, as described in the International Reference of Preparation, distributed by the National Institute for Biological Standards and Control, Holly Hill, London. Compounds having significantly enhanced half-lives may be administered at lower doses.

The invention is further illustrated by the following non-limiting examples.

EXAMPLES

Example 1

Preparation of ZG 2807 Natural Product Sample

Samples from the Culture and Metabolites Collection of Novo Nordisk were prepared as follows: Three milliliters of a spore/mycelium suspension of ZG 2807 was used to inoculate 100 ml YES medium (150 g/l sucrose; 20 g/l yeast extract (Difco, Detroit, Mich.); 0.0178 g/l $ZnSO_4 \cdot 7H_2O$; 0.0078 g/l $CuSO_4 \cdot 5H_2O$, pH 6.4) in 250 ml baffle shake flasks. The flasks were shaken at 200 RPM for 12 days at 26° C. The whole broth (100 ml) was homogenized then mixed with an equal volume of ethyl acetate (EtOAc). Extraction was allowed to proceed for 16–18 hours at room temperature with stirring. The extract was then centrifuged at 1500 g for 10 minutes to separate the EtOAc and aqueous layers. The EtOAc layer was collected and evaporated to dryness in a rotary evaporator, and redissolved in either 2 ml methanol or a volume of DMSO (dimethylsulfoxide) equal to 1/14 of the original broth volume (making the extract concentration 14X the original broth concentration). The solution was flushed with argon for 5 minutes, and 1 ml aliquots were transferred to argon-filled vials and stored at −80° C. When extracts are needed, the vials are thawed at room temperature, and the samples are removed with a disposable hypodermic syringe by perforation of the rubber membrane. The material may be re-stored at −80° C.

Example 2

Calcitonin Mimetic Assay Development

A. Creation of CRE-Luciferase Cell Line: BHK/KZ10-20-48

Creation of this cell line is described in pending U.S. patent application Ser. No. 08/100,887 which is incorporated herein in its entirety. Briefly, a baby hamster kidney cell line, BHK 570 (deposited with the American Type Culture Collection, 12301 Parklawn Dr., Rockville, Md. under accession number CRL 10314) which does not express calcitonin receptor, was identified. This cell line was transfected using calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973) with a plasmid pKZ10 (disclosed in pending U.S. patent application Ser. No. 08/100,887) encoding a luciferase reporter gene (de Wet et al., *Mol. Cell. Biol.* 7:725–37, 1987; Braiser et al., *Biotechniques* 7:1116–22, 1989) under the control of cAMP response elements (CRE) (Comb et al., *Nature* 323:353–56, 1986; Belegeane et al., *Mol. Cell. Biol.* 7:3994–4002, 1987; Roesler et al., *J. Biol. Chem.* 263:9063–66, 1988; Yamomoto et al., *Nature* 334:494–98, 1988; Montimny et al., *Metabolism* 39(9, Suppl 2):6–12, 1990; and Habener et al., *Metabolism* 39(9, Suppl 2):13–16, 1990), as well as a DHFR selectable marker. Stable transfectants were selected by growth in Dulbecco's modified Eagle's medium (DMEM) supplemented with 10% heat inactivated fetal bovine serum (HI-FBS), 2 mM L-glutamine and 1 mM sodium pyruvate containing 250 nM methotrexate (MTX) for 10–14 days. Clones were isolated, grown to confluence in opaque white microtiter plates (Dynatech, Chantilly, Va.), then treated with 25 mM forskolin, which elevates cellular cAMP through direct activation of adenylate cyclase (Berkowitz and Gilman, *Proc. Nat. Acad. Sci. USA* 87:5258–62, 1990) for 4 hours at 37° C., 5% $CO_2$. Following incubation, cells were lysed and assayed for luciferase induction in a Labsystems Luminoskan microtiter luminometer (Labsystems Inc., Morton Grove, Ill.) using a Promega luciferase kit (El500, Promega Corp., Madison, Wis.), as described below. Clones demonstrating significant induction of CRE-luciferase expression in response to forskolin, as compared to unstimulated (basal) luciferase expression, were retested, and clone KZ10-20-48 with a 20 fold (range 15–25 fold) induction of CRE-luciferase was selected.

B. Creation of human calcitonin receptor/CRE-Luciferase Cell Line: Hollex-1

Receptor positive cell line

KZ10-20-48 was transfected, using calcium phosphate-mediated transfection (as described above), with pHollex encoding a human calcitonin receptor cDNA (cloned from a cDNA library derived from T47D human mammary tumor cells (ATCC, HBL 133), as described in pending U.S. patent application Ser. No. 08/100,887) and a neomycin selectable marker. Stable transfectants were selected following 10–12 days growth in DMEM supplemented with 10% HI-FBS, 2 mM L-glutamine, 1 mM sodium pyruvate, 250 nM MTX and containing 1 mg/ml G418. Clones were isolated, grown to confluence in opaque white Dynatech microtiter tissue culture plates, then treated with 1 μM human calcitonin or 25 mM forskolin for 4 hours at 37° C., 5% $CO_2$, and assayed for luciferase induction as described below. Clones demonstrating significant induction of CRE-luciferase in response to human calcitonin were re-screened following treatment with human calcitonin at concentrations ranging from 0.001–1000 nM, and clone Hollex-1 with a 20 fold (range 10–25 fold) induction of luciferase, a human calcitonin EC50 of 0.02 nM, and a forskolin EC50 of 1.2 μM, was selected for use in the high throughput screening assay for calcitonin mimetics.

Receptor negative cell Line

KZ10-20-48 was also transfected with plasmid Zem 228 lacking the human calcitonin receptor gene, and the resulting transfectant pool, KZ10-20-48/Zem 228, was isolated for use as a receptor-negative specificity control for substances found to induce luciferase expression in Hollex 1 in the primary screen. Forskolin induces CRE-luciferase in KZ10-20-48/Zem 228 by 30 fold (range 20–35 fold) with an EC50 of 0.6 μM (range 0.5–1.5 μM), while human calcitonin at concentrations up to 1000 nM fails to induce CRE-luciferase levels above the basal level of expression Care was taken to select calcitonin receptor-positive and -negative clones that had similar CRE-luciferase inducibility, as demonstrated by forskolin dose responses that were essentially superimposable for the two cell lines. This criteria ensured that even small magnitude differences in response to test substances of calcitonin receptor-positive cells over calcitonin receptor-negative cells would be meaningful.

C. Creation of hamster calcitonin receptor/Luciferase Cell Line: Boris/KZ10-3

An alternative cell line expressing the hamster calcitonin receptor was isolated for use in calcitonin mimetic screening. BHK 570 cells were transfected with the human cDNA library derived from T47D cells in plasmid vector Zem 228. Stable transfectants were isolated following 10–12 days growth in G418.

Colonies were tested for their ability to bind $^{125}$I-human calcitonin. The cells were plated at a density of $1 \times 10^5$ cells/well in a 24-well cell culture dish and allowed to grow for 48 hours at 37° C. and 5% $CO_2$ in DMEM supplemented with 10% HI-FBS, 2 mM L-glutamine, 1 mM sodium pyruvate, and 1 mg/ml G418. The cells were rinsed in binding medium (500 ml RPMI 1640 (Sigma, St. Louis, Mo.), 1 mg/ml BSA (Boehringer Mannheim, Indianapolis, Ind.)) to remove serum. Three hundred microliters of binding medium containing radiolabeled $^{125}$I human calcitonin (binding only or competition also) were added to appropriate wells. The cells were incubated for 1.5 hours at room temperature, and then rinsed 3 times with PBS to remove unincorporated radioactivity. Five hundred microliters of 1 N NaOH was added to each well to solubilize the cells. The samples were collected from each well and CPMs were counted on a gamma counter.

One clone, Boris, with high calcitonin receptor expression was re-transfected with pKZ10, as described above, and stable transfectants were isolated following 10–14 days growth in DMEM supplemented with 10% HI-FBS, 2 mM L-glutamine, 1 mM sodium pyruvate, 250 nM MTX and 1 mg/ml G418. Clones were isolated and screened for induction of luciferase expression by human calcitonin or forskolin, as described below. Clone Boris/KZ10-3, with a 30 fold (range 25–40X) induction of luciferase in response to human calcitonin, was selected for use in high throughput screening for calcitonin mimetics. Boris/KZ10-3 had a 25 fold (range 0.7–1.5 µM) response to forskolin (EC50=0.9 µM).

The human calcitonin receptor negative clone KZ10-20-48/Zem 228, described above, was used as a specificity check for substances found to induce luciferase expression in Boris/KZ10-3 during primary screens.

D. Creation of human Glucagon Receptor/CRE-Luciferase Cell Line: KZ10-20-48/pLJ6-4-25

Test substances that appeared to specifically increase luciferase induction in calcitonin receptor-positive cells, but not calcitonin receptor-negative cells, were subjected to an additional specificity check, i.e., their inability to activate other members of the G-protein coupled-receptor family. The glucagon receptor is another member of the G-protein coupled receptor family that transduces signal through adenylate cyclase mediated elevation of cAMP (Robison et al., Cyclic AMP, Academic Press, New York, 1971; Jelinek et al., Science 259:1614–16, 1993). KZ10-20-48 was transfected, as above, with pLJ6' (deposited with the American Type Culture Collection, 12301 ParkLawn Drive, Rockville, Md. 20852, under Accession Number 69183) as disclosed in pending U.S. patent application Ser. No. 08/086,631, containing the human glucagon receptor cDNA in plasmid pHZ-1, which also contains a DHFR selectable marker. Stable transfectants were selected in DMEM supplemented with 10% HI-FBS, 2 mM L-glutamine, 1 mM sodium pyruvate, 250 nM MTX and 1 mg/ml G418, and were screened for CRE-luciferase induction in response to 25 mM forskolin or 1000 nM human glucagon (Sigma), as described below. Clone KZ10-20-48/pLJ6-4-25 was selected for use in specificity confirmation. This clone exhibits a 35 fold induction of luciferase in response to human glucagon (EC50=0.2 nM) or forskolin (EC50=2.1 µM).

Example 3

CRE-Luciferase Assay Method for Calcitonin Mimetics

Receptor-positive and -negative cell lines were maintained by serial passage in growth medium (DMEM supplemented with 10% HI-FBS, 2 mM L-glutamine, 1 mM sodium pyruvate, 250 nM MTX, and 1 mg/ml G418). On the day prior to assay, cells were trypsinized, adjusted to $2 \times 10^5$ cells/ml in growth medium, plated in opaque white Dynatech Microlite microtiter tissue culture plates at 100 µl/well ($2 \times 10^4$ cells), and grown overnight to confluence, 37° C., 5% $CO_2$.

Test substances were prepared in $H_2O$ or DMSO at 100 times the final desired assay concentration. Induction was initiated by removing spent medium from the wells and adding 100 µl/well test substance diluted 1:100 or 1:1000 (first round screening extracts were diluted 1:1000) in assay medium (DMEM supplemented with 10% HI-FBS, 2 mM L-glutamine, 1 mM sodium pyruvate and 10 mM Hepes pH 7.25). Controls were included on each plate: untreated wells (basal), 25 mM forskolin, and 100 nM human calcitonin. If test substances were prepared in DMSO, then an equal concentration of DMSO was included in control wells (not to exceed a final assay concentration of 2% DMSO, with a preferred maximum of 1%). Plates were incubated for 3 to 8 hours (4 hours preferred) at 37° C., 5% $CO_2$.

Luciferase induction was measured using a Promega luciferase assay kit (E1500) according to the assay kit protocol. Briefly, assay medium was removed and cells were washed once with phosphate buffered saline (PBS). After the wash, 25 µl of lysis buffer was added to each well, and the plates were incubated for 15 minutes at room temperature. The plates were transferred to a Labsystems Luminoskan microtiter luminometer which added 40 µl/well Luciferase Assay Substrate (Promega Corp.). The amount of luminescence (relative light units, RLU) was determined following a 1 second mix and a 1–3 second integration of signal. Basal (uninduced) luciferase signal was subtracted from all measurements, and the luciferase signal induced by test samples was expressed as a percentage of the signal in the calcitonin and forskolin controls. Specificity of the luciferase induction for calcitonin receptor-positive cell lines was determined by comparing the percent control values in the calcitonin receptor-positive lines (Hollex-1 or Boris/KZ10) to those observed in the calcitonin receptor-negative cell line (KZ10-20-48/Zem 228) and in the glucagon receptor-positive cell line (KZ10-20-48/pLJ6'-4). Samples inducing a signal over the basal level were selected for further characterization.

For ZG 2807, luciferase induction was 8.6% of the control level (human calcitonin) in Boris/KZ10-3 while only 0.4% of control in calcitonin receptor negative KZ10-20-48/Zem 228. Subsequently, a dose response of ZG 2807 was tested on the calcitonin receptor positive line, Boris/KZ10, alongside the calcitonin receptor negative cell line, KZ10-20-48/Zem 228. A maximum luciferase induction of 25.9% was observed on the receptor positive cell line at a 1:100 dilution of extract, while the maximum luciferase induction observed on the receptor negative cell line was 0.3%. Based on these results, the purification of the active compound(s) from this extract was undertaken, guided at all steps by the CRE-luciferase assay on both the receptor positive and negative cell lines.

TABLE 1

Effect of Calcitonin Mimetics on the Induction of CRE-Luciferase in BHK 570 Cells Expressing Human Calcitonin Receptor and a CRE-Luciferase Reporter

| Calcitonin Mimetic | CRE-Luciferase Induction $EC_{50}$ (nM) |
|---|---|
| ZG 2807 A (SEQ. ID. NO. 1) | 506 |

TABLE 1-continued

Effect of Calcitonin Mimetics on the Induction of
CRE-Luciferase in BHK 570 Cells Expressing Human
Calcitonin Receptor and a CRE-Luciferase Reporter

| Calcitonin Mimetic | CRE-Luciferase Induction $EC_{50}$ (nM) |
|---|---|
| ZG 2807 B (SEQ. ID. NO. 2) | 525 |

For comparative purposes, the EC50 for human calcitonin is about 0.02 nM and for salmon calcitonin is about 0.006 nM.

Example 4

Direct cAMP Measurement by RIA/SPA Assay

Cell lines were prepared as in Example 3 above. At the time of assay, growth medium was removed and replaced with 50 µl/well of test sample, forskolin, or human calcitonin in assay medium (DMEM supplemented with 10% HI-FBS, 20 mM Hepes pH 7.2, and 10 µM 3-Isobutyl-1-methylxanthine (IBMX) (Sigma)) pre-warmed to 37° C. Cells were incubated for 10 minutes at 37° C., 5% $CO_2$, followed by addition to each well of 200 µl water heated to just below the boiling point. After 15 minutes at room temperature, the supernatants were collected and transferred to a new microtiter plate and stored at −20° C. until assayed for cAMP. cAMP concentrations were determined using a radioimmunoassay scintillation proximity assay (SPA) kit (RPA 538) (Amersham Corp.) following the acetylation protocol described in the package insert. Alternatively, a conventional cAMP RIA assay may be used (Steiner et al., *J. Biol. Chem.* 247:1106–13, 1972; Harper and Brooker, *J. Cyc. Nucl. Res.* 1:207–18, 1975). The basal (uninduced) cAMP level in untreated cells was subtracted from all treated samples. The concentration of cAMP induced by test substances was expressed as a percentage of the cAMP concentration induced by forskolin or human calcitonin.

Example 5

Bone Resorption

A. Calvarial Assay

Calvaria from 4-day old neonatal CD-1 mice (pregnant mice received from Charles River Laboratories, Wilmington, Mass.) were trimmed with fine-tipped scissors to leave the parietal regions, including the sagittal suture. These trimmed bones were placed singly per well into 6-well cell culture cluster plates (Costar, Pleasanton, Calif.) with 1 ml/well of growth medium (DMEM, BioWhittaker, Walkersville, Md.) with 4.5 g/L glucose, 0.29 mg/ml L-glutamine, 1 mM sodium pyruvate, 15% heat-inactivated horse serum, and antibiotics (penicillin-G 50 µg/ml, streptomycin 50 µg/ml, and neomycin 100 µg/ml), and rocked gently (RedRocker™, model PR50-115V, Hoefer, San Francisco, Calif.) at 37° C. in a 5% $CO_2$ humidified incubator for 24 hours preincubation.

Following incubation, medium was removed and replaced with 1.5 ml/well of growth medium containing 1 nM parathyroid hormone (PTH) 1-34 (Sigma) to stimulate bone resorption. For evaluation of the ability of calcitonin mimetics to inhibit PTH induced bone resorption, mimetic compounds in DMSO were added to the growth medium at concentrations ranging from 1–240 µg/ml (final assay concentration of DMSO less than or equal to 1%). In each experiment human calcitonin (0.02–20 nM, 0.2–2 nM preferred) was added to PTH treated bones as a positive control. Control wells that did not receive PTH, human calcitonin or calcitonin mimetic were included for determination of calcium release from untreated bones. All control wells contained a final assay concentration of DMSO equal to that present in calcitonin mimetic treated wells.

Five bones were included in each sample group. Bones were incubated for 72 hours following PTH addition to allow resorption of bone to occur. Observations were made of the general appearance, healthiness and number of cells that migrate from the calvaria during the incubation as a possible indication of possible toxicity. Calvaria to be examined histologically were transferred to glass scintillation vials containing 10 ml of 10% neutral buffered formalin. The medium was removed from the wells, and total calcium measurements were made using a Nova 7/7+7 Electrolyte Analyzer (Nova Biomedical, Waltham, Mass.) according to the manufacturer's specifications. Induction of bone resorption by PTH is seen as an increase in the concentration of calcium in the growth medium due to degradation of the bone matrix. Human calcitonin and biologically active calcitonin mimetics inhibit this bone resorptive process as demonstrated by a lowering of the calcium in growth medium as compared to bones treated with PTH alone.

B. Calvaria Histology

To confirm the findings in the calvarial bone resorption assay employing calcium release from culture mouse calvariae, selected bones were fixed in 10% neutral buffered formalin and demineralized in 5% formic acid with 5% formalin. The bones were dehydrated through an ascending series of ethanol concentrations, infiltrated in glycol methacrylate, and embedded using a JB-4 embedding kit (PolySciences, Warrington, Pa.) (Liu and Kalu, *J. Bone Miner. Res.*, 5:973–82, 1990). Cross sections of calvariae cut at 5 µm were obtained and stained for tartrate-resistant acid phosphatase (TRAP) activity and counterstained with methyl green and thionin for cell morphology (Liu and Kalu, *J. Bone. Miner. Res.* 1990, supra). Osteoclasts were identified by TRAP stain, multinucleation, large cell size, and irregular cell shape. The number of osteoclasts were counted from endocranial and ectocranial bone surfaces and expressed as number/mm perimeter. The size of all the osteoclasts counted was also measured using a Bone Morphometry program (Lui and Kalu, supra.; Bain et al., *J. Done Miner. Res.* 8:435–42, 1993). This histomorphometric method demonstrated increases in the number and size of osteoclasts due to human parathyroid hormone (PTH 1-34) treatment. This PTH-induced increase was suppressed by treatment with human calcitonin.

Calcitonin mimetic compounds were evaluated in a similar fashion for their ability to suppress PTH-induced increases in osteoclast number and size. Cell toxicity (or death) was also evaluated morphologically. A low level of toxicity was indicated by the appearance of pyknotic nuclei in a small number of bone cells. With an increased level of toxicity, a further increase in the number of these pyknotic nuclei, detachment of cells from bone surfaces, and losses of cytoplasmic stain and cell boundaries were observed. The osteocytic space also appeared empty.

TABLE 2

Effect of Calcitonin Mimetics on PTH-Induced Bone Resorption in Mouse Calvariae

| Calcitonin Mimetic | EC$_{50}$ (µM) | Inhibition of Ca++ Release Histology |
|---|---|---|
| ZG 2807 A (SEQ. ID. NO. 1) | 33.2 | Inhibition of osteoclast size |
| ZG 2807 B (SEQ. ID. NO. 2) | 38.4 | Inhibition of osteoclast size |

For comparative purposes, the EC50 for human calcitonin is about 0.2 to 0.5 nM.

Example 6

Re-Fermentation procedure

Revival from a "glycerol bank": One vial of the frozen ZG 2807 culture (a 1:1 mixture of glycerol and a 2-day culture grown in YES medium) was removed from the freezer and allowed to thaw in a laminar flow hood.

For agar inoculation, 500 µl of the thawed ZG 2807 stock solution was inoculated onto 100 ml Potato Dextrose Agar (PDA) (Difco) in a 250 ml Erlenmeyer flask to form a seed culture. Sterile water (500 µl) was added onto the agar to aid in the spreading of the culture solution. The flasks were then incubated at 26° C. for one week. After one week of incubation on PDA, no sporulation of the ZG 2807 culture was observed, but filamentous growth was seen. One hundred milliliters of sterile water was added to the flask and mixed well with a sterile pipette. The suspension was used to inoculate 500 ml baffle flasks (3.0 ml/flask) containing 100 ml of YES medium. The flasks were then shaken (150 RPM) at 26° C. for 12 days.

For liquid inoculation, 500 µl of a thawed ZG 2807 stock solution was inoculated into 100 ml YES medium in 500 ml baffled shake flask to form a seed culture. The flask was then shaken (200 RPM) at 26° C. for 2 days. Mycelial growth was indicated by the production of light orange pigmentation. After 2 days incubation in YES medium, the suspension was used to inoculate 500 ml baffle flasks (3.0 ml/flask) containing 100 ml YES medium. The cultures were then grown as above.

Example 7

Isolation and purification of 2807 A and 2807 B

A. Instrumentation

Preparative HPLC was carried out on a Rainin Dynamax system (Rainin Instrument Co. Inc., Emeryville, Calif.) with an HPLC solvent delivery setup utilizing 50 ml pump heads, a pressure module, and a Dynamax dual chamber dynamic mixer. Heat tape attached to a variable autotransformer at 120V was used to heat the column and the aqueous phase, and a Rheodyne 7125 syringe loading sample injector was used to introduce the sample. A Rainin UV-D II dual wavelength detector set at 220 and 280 nm was used to monitor the chromatography, and fractions were collected either manually or with a Rainin Dynamax FC-2 fraction collector. Analytical HPLC was carried out on a HP1090 liquid chromatograph (Hewlett Packard, Wilmington, Del.) run with the HP ChemStation (Pascal series) software. UV spectra were recorded on a DU 640 spectrophotometer (Beckman, Fullerton, Calif.). Optical rotations were obtained on a Jasco DIP-370 Digital Polarimeter (Jasco Inc., Easton, Md.). IR spectra were recorded on a Perkin Elmer 1600 FTIR series detector. Melting points were determined with a Mel-Temp II melting point apparatus (Laboratory Devices, Inc., Holliston, Mass.) and are uncorrected.

B. Isolation

Re-fermentation broth ZG 2807 was centrifuged in a J6 MI centrifuge (Beckman, Fullerton, Calif.) at 3500 RPM for 20 minutes. Ethanol was added to the mycelial cake in a 1:1 (V:V) ratio, and the mixture was shaken at 200 RPM (throw=2) for 2 hours. The ethanol was separated from the mycelium by centrifugation at 3500 RPM for 20 minutes. The ethanol was removed in vacuo and the ethanol extract was tested for calcitonin-like activity by measuring luciferase induction using the CRE-luciferase assay, for example, as described above. The yield of ethanol extract was 9.2 g/l of fermentation broth.

Up to 20 g of this material was then re-dissolved in 270 ml methanol and 30 ml H$_2$O and extracted three times with 100 ml hexane. The hexane extracts were pooled and evaporated to dryness (P1 fraction). An additional 147.5 ml of H$_2$O was added to the aqueous layer and extracted three times with 100 ml chloroform. The chloroform layers were pooled and evaporated to dryness (P3 fraction, yield of 440 mg/l of fermented broth). The remaining aqueous layer was evaporated to dryness (P4 fraction).

The P1, P3, and P4 solvent partition fractions were assayed for luciferase induction, as outlined above. Luciferase induction was seen in the P3 fraction. One gram of the P3 fraction was dissolved in 6 ml methanol. To the methanol solution was added 6 ml water, 8 ml ethyl acetate, and 7 ml hexane. The two phases were separated and evaporated to dryness. The lower phase, which had a yield of 260 mg/l of broth, was found to induce luciferase activity as measured by the CRE-luciferase assay. The dried residue of the lower phase (1 g) was dissolved in methanol and loaded onto the top of a column (40 mm ID×300 mm) of C-18 silica gel (40 µ). Vacuum was applied to the end of the column, and fractions were eluted using a step gradient of 20%, 40%, 60%, 80% and 100% acetonitrile (CH$_3$CN)/0.05% TFA (three column volumes each).

Each fraction was subjected to the CRE-luciferase assay, as described above. The 60% fraction, with a yield of 95 mg/liter of broth, had the greatest luciferase induction. This material was subjected to preparative reverse phase chromatography using a Vydac C-18 column (Hewlett Packard, Wilmington, DE) (22×250 mm, 10 µm) heated to 45° C., as described above. Ninety five milligrams of the material was dissolved in 5 ml of 40% (CH$_3$CN)/0.05% TFA and loaded onto the column. The column was eluted with 45% CH$_3$CN/0.05% TFA over 40 minutes to separate two major components at retention times 25 minutes and 30 minutes (2807 A and B, respectively). 2807 A gave a 5% yield of the injected material, equal to 4.8 mg, and 2807 B gave an 11% yield, equal to 10.5 mg. The partially purified fractions were individually re-injected (5–10 mg/injection) for the final purification step, using the same method as described above, with a final yield of 2.8 mg/l of 2807 A and 5.3 mg/l of 2807 B.

After evaporation, fractions 2807 A and B were obtained as white powders which were readily soluble in methanol, ethanol, n-butanol and dimethyl sulfoxide; slightly soluble in acetonitrile, ethyl acetate, and chloroform; and insoluble in hexane.

UV(MeOH) $\lambda_{max}$ 206 nm ($\epsilon$ 37000), 217 nm ($\epsilon$ 29000), 280 nm ($\epsilon$ 3700) and 289 nm (s 3200) for 2807 A and B.

$[\alpha]_D^{26}=4.5°$ (c 1, methanol) for 2807 A and $[\alpha]_D^{26}0°$ for 2807 B.

IR(KBr) $v_{max}$ 3316, 2963, 1654, 1534, 1458, 1420, 1202, 1179 cm$^{-1}$.

M. P. 116°–124° C. with decomposition for both 2807 A and B.

Example 8

Amino Acid Analysis of fractions ZG 2807 A and ZG 2807 B

Fractions 2807 A and B were each hydrolyzed for 22 hours in 6N HCl/2% phenol at 112° C. The amino acids were then analyzed on a Beckman 6300 amino acid analyzer. This machine is designed for ion exchange separation followed by post column ninhydrin derivatization and uses a Beckman sodium-based 4 mm×12 cm high performance column and sodium citrate buffers. A three step pH and three step temperature gradient were used in the normal run program. System Gold version 3.1 software (Beckman) was used for data acquisition. The following compositions were determined for each fraction:

| Amino Acid | # Residues |
| --- | --- |
| Sample: ZG 2807A | |
| Threonine | 1 |
| Glu or Gln* | 2 |
| Proline | 2 |
| Glycine | 1 |
| Isoleucine | 1 |
| Leucine | 1 |
| Phenylalanine | 1 |
| Sample: ZG 2807B | |
| Threonine | 1 |
| Glu or Gln* | 2 |
| Proline | 2 |
| Glycine | 0 |
| Isoleucine | 1 |
| Leucine | 1 |
| Phenylalanine | 1 |

*Note: during hydrolysis glutamine is changed to glutamic acid.

Example 9

MS Analysis (Q1 scan)

Electrospray mass spectral analysis was performed on each peptide, 2807 A and B, using a Sciex API III triple quadrupole mass spectrometer fitted with an articulated ionspray plenum and an atmospheric pressure ionization source (SCIEX, Thornhill, Ontario).

The mass spectrometer was tuned and calibrated using a mixture of polypropylene glycols (PPG) (425, 1,000, and 2,000 at $3.3\times10^{-5}$ M, $1\times10^{-4}$ M, and $2\times10^{-4}$ M, respectively) in 50/50/0.1 H$_2$O/methanol/formic acid (v/v/v), 1 mM NH$_4$OAc. Normal scan electrospray mass spectrometry (ESMS) was recorded at instrument conditions sufficient to resolve isomers of the PPG/NH$_4^+$ doubly charged ion at m/z 520 (85% valley definition).

Five microliters of each sample was injected onto the mass spectrometer via a solvent of 50% MEOH/H$_2$O/0.2% formic acid. The mass spectrometer was scanned over a range of m/z 350–2250, with a dwell time of 0.5 and a step size of 0.2 amu. The orifice potential was set at 65 V.

The masses determined for each peptide by mass spectral analysis and amino acid analysis are compared below:

| Sample MS | Analysis | Amino Acid Analysis | MASS DIFF |
| --- | --- | --- | --- |
| ZG 2807B | 1807 | 945(if 2 × Glu) or 944(if 1 × Glu and 1 × Gln) or 943(if 2 × Gln). | 862,863,864 |
| ZG 2807A | 1864 | 1002(if 2 × Glu) or 1001(if 1 × Glu and 1 × Gln) or 1000(if 2 × Gln). | 864,863,864 |

The mass difference between the two peptides is 57 amu, which corresponds to a gly and concurs with the amino acid analysis.

The difference in mass between the ms data and the amino acid analysis indicated that there were some amino acids that were not resolved by amino acid analysis. To determine what these amino acids were, the peptide was sequenced by Edman degradation (Edman and Begg, Eur. J. Biochem. 1:80–91, 1967) and by collision induced dissociation (Johnson et al., Anal. Chem. 59:2621–25, 1987) on the Sciex API III analyzer. Edman degradation revealed no sequence, indicating that the N-terminus of each peptide was blocked.

Example 10

MS/MS Analysis

A. Peptide ZG 2807 B

Since there was more material available, ZG 2807 B was analyzed first. Fragmentation of the singly charged parent ion, 1808.2, resulted in two fragment ions, 1038.8 and 769.4. These ions represent the N-terminal and the C-terminal portion of the parent ion, 1808.2. A daughter scan of m/z 1038.8 and 769.4 was analyzed to further fragment the peptide and obtain sequence information.

M/Z 769.4 fragmented into two ions, 493 and 277. MS/MS of m/z 493 fragmented into five different ions, 408, 311, 226, 198, and 70. The mass difference of 493-408 is equal to 85 amu. This is the mass of either 2-aminoisobutyric acid (Aib) or 2-aminobutyric acid (Abu). Both of these amino acids are found in natural products. The mass difference of 408-311 is equal to 97 amu, which is equal to a proline. The mass difference of 311-226 is equal to 85 which is equal to either aminoisobutyric acid or 2-aminobutyric acid. M/Z 226 was fragmented further into the following ions: 198, 129, 101, 84, and 70. M/Z 84, 101, and 129 are the low mass immonium ions of either lysine or a glutamine. Since lysine was not found in the amino acid analysis and glutamine was, these immonium ions must represent a glutamine. M/Z 70 is the low mass immonium ion for proline. M/Z 70 (–28 amu from B-ions) represents the A1 ion and m/z 198 represents the A2 ion, meaning that proline is N-terminal to glutamine, which is N-terminal to the rest of the sequence of the fragment, 769.4. The predicted sequence is Pro-Gln-Aib(or Abu)-Pro-Aib(or Abu). M/Z 277 is the C-terminal fragment of m/z 769.4. MS/MS of 277 showed a low mass immonium ion of 120, which is indicative of a phenylalanine. Mass 277-1 amu(H$^+$)-147 amu(Phe) -18 amu (H$_2$O)=111 amu. The spectrum there is a low mass immonium ion of 84, which would represent the mass of 111 minus the carboxyl group(CO) plus 1 amu (H$^+$)=84. The amino acids corresponding to mass 111 amu are pyroglutamic acid, 2-piperidinecarboxylic acid (Pip), or methyl proline (MePro). Pyroglutamic would be found at the N-terminal portion of the molecule, so it would be eliminated from these choices. Methyl proline is the likely candidate. The predicted sequence for the fragment ion 769.4 is the following: Pro-Gln-Aib(or Abu)-Pro-Aib(or Abu)-MePro.

MS/MS analysis was performed on ion 1039, which fragmented completely into eight different B ions. The fragment ions are as follows:

| Mass Difference | Amino Acid   | B ion  |
| --------------- | ------------ | ------ |
| 1039            | Aib (or Abu) | $B_9$  |
| 953.8           | Ile          | $B_8$  |
| 840.6           | Aib (or Abu) | $B_7$  |
| 755.41          | Thr          | $B_6$  |
| 654.4           | Leu          | $B_5$  |
| 541.2           | Aib (or Abu) | $B_4$  |
| 456.2           | Gln          | $B_3$  |
| 328.4           | Val          | $B_2$  |
| 229.2           | Ac—Trp       | $B_1$  |

MS/MS analysis of m/z 328.4 fragmented into the $A_1$ ions for Ac-W (mass 201;229-28=201). Also, present in the spectra was the low mass immonium ion for valine. Tryptophan would not show up in the amino acid analysis due to the fact that it is destroyed during acid hydrolysis.

Amino acid analysis of the two standards for 2-aminoisobutyric acid and aminobutyric acid (Bachem Biosciences, Inc., King of Prussia, Pa.) showed that the retention time and intensity of the peak of 2-aminoisobutyric acid was found to be the same as that in the amino acid analysis of the peptide ZG 2807 B. The recovery of aminoisobutyric acid was low as compared to the same molar ratio of aminobutyric acid. Valine was not detected in the amino acid analysis, so this amino acid likely is isovaline rather than valine.

In order to clarify the order of the two most C-terminal residues on the peptide m/z 1807, the peptide was methylated. The mass of the peptide shifted to 1821, indicating that only one methyl ester was added to the C-terminal carboxylic acid, and that no acidic amino acids are present, such as glutamic acid or aspartic acid, unless the C-termini is blocked (this also agrees with the predicted sequence and the amino acid analysis). MS/MS analysis of the methylated vs. non methylated peptide showed that the methyl ester spectrum differed only by the presence of an ion at M/Z=180. M/Z 180 is the $Y_1$ ion for phenylalanine and indicates that phenylalanine is at the C-terminus.

The predicted sequence of peptide ZG 2807 B is as follows: AcTrp-isoVal-Gln-Aib-Leu-Thr-Aib-Ile-Aib-Pro-Gln-Aib-Pro-4MePro-Phe-OH

B. Peptide ZG 2807 A

The amino acid analysis and mass spectral analysis showed that this peptide differed from ZG 2807 B by only a glycine. MS/MS analysis of this peptide was performed to show the position of the glycine.

The spectral analysis differed from peptide ZG 2807 B by the non-existence of m/z 166, which is the Y1 ion for phenylalanine and the presence of m/z 76, which is the Y1 ion for glycine (57(glycine) +18($H_2O$)+1($H_+$)=76. The $Y_2$ ion for phenylalanine (M/Z 223) was present. This indicates that phenylalanine is not at the C-terminal position.

The predicted sequence of peptide ZG 2807 A is as follows: AcTrp-isoVal-Gln-Aib-Leu-Thr-Aib-Ile-Aib-Pro-Gln-Aib-Pro-4MePro-Phe-Gly-OH

Example 11

NMR

All NMR were run on either a Varian 500 or 600 MHz Unity-plus spectrometer at a sample concentration of 18 mg in 650 μ. DMSO-d6 was used as both solvent and reference. The structure was determined using a combination of one and two dimensional NMR experiments in conjunction with the mass spectral data and the amino acid analysis. A one dimensional $^1$H-NMR, an HMQC (heteronuclear multiple quantum correlation-inverse detected) (Marion et al., *J. Magn. Reson.* 85:393, 1989), and a DQFCOSY (phase sensitive-double-quantur filtered COSY) (Piatini et al., *J. Am. Chem. Soc.* 104:6800–01, 1982; Rance, et al., Biochem. Biophys. Res. Comm. 117:479–85, 1983), were run on a Varian Unity-plus 500 MHz NMR (at the Varian NMR applications lab in Palo Alto, Calif.). A TOCSY (total correlation spectroscopy) (Levitt et al., *J. Mag. Reson.* 65:328, 1982; Bax and Davis, *J. Magn. Reson.* 65:355, 1985), and a ROESY (rotating frame overhauser experiment) (Kessler et al., *J. Am. Chem. Soc.* 109:607–09, 1987), were performed on a Varian Unity-plus 600 MHz NMR (also at the Varian NMR applications lab in Palo Alto, Calif.). A one dimensional 13C-NMR and a DEPT (distortionless enhancement through polarization transfer) (Doddrell, et al., *J. Mag. Reson.* 48:323, 1982), completed the suite of NMR experiments run on this molecule. These experiments were run on a Varian Unity-plus 500MHz NMR spectrometer at ZymoGenetics, Seattle, Wash. The DQFCOSY, TOCSY, and ROESY experiments were run using the States-Haberkorn hypercomplex phase sensitive method (States et at., *J. Magn. Reson.* 48:286–92, 1982).

The $^1$H-NMR indicated a peptidal compound based upon the downfield NH signals between 6.8–8.5 ppm, which showed correlations to the c-αH signals between 3.5–4.5 ppm in the DQFCOSY experiment. An amino acid analysis indicated the presence of the following amino acids in ZG-2807 A: 1 threonine, 2 glutamines (or glutamic acids), 2 prolines, 1 isoleucine, 1 leucine, 1 phenylalanine, and 1 glycine. Electro-spray mass-spectral analysis of this compound gave an (M+H)+ of 1864.09.

The lack of NH-CαH correlations in the DQFCOSY (8 when there should have been approximately 15–16 based upon mass spec), and the presence of a large packet of singlet methyl signals around 1.3 ppm (determined from the HMQC experiment), indicated the presence of α-aminoisobutyric acid residues. This was confirmed by another amino acid analysis in which a 2-aminoisobutyric acid standard (Bachem) was shown to elute in the same position as a previously unidentified peak.

Since Edman degradation failed to work on this molecule, it was postulated that the structure was either a cyclic peptide or a linear peptide blocked at the N-terminus. Mass spectral analysis performed on ZG-2807 B (which was assumed to be the same sequence as ZG-2807 A minus a glycine) indicated the presence of a facile cleavage site in the molecule. This allowed the sequencing of two fragment ions of 1038 and 769 amu by MS—MS. This information, in conjunction with the knowledge that there had to be a tryptophan residue complete with an amide proton based upon the DQFCOSY data, allowed the following tentative sequence to be assigned: Ac-Trp-Val(or Iva)-Gln-Aib-Leu (or Ile)-Thr-Aib-Ile(or Leu)-Aib-Pro-Gln-Aib-Pro-Aib-MePro(or Pip)-Phe. A free carboxy terminus was postulated due to the addition of 15 amu on that dipeptide residue that resulted upon methylation with diazomethane. An N-terminus acetyl group was postulated because of the good fit to a tryptophan residue plus 45 amu at that position. These assignments gave a good fit to a molecule formula of $C_{89}H_{136}N_{19}O_{21}$.

TOCSY and a ROESY experiments, in conjunction with the DQFCOSY data showed the presence of an isovaline rather than a valine residue in position 2. There was an ethyl group correlation in the DQFCOSY of δ 1.92 ppm and δ1.64 ppm, which were not coupled to anything else. A three proton singlet at δ1.27 ppm could then be assigned to an isovaline β-methyl based upon ROESY correlations to the glutamine NH proton at δ8,123 ppm. ROESY correlations from the isoleucine C-αH at δ3.83 ppm to the threonine NH at δ7,580 ppm as well as from the isoleucine D proton at δ1.46 ppm to the C-αH of threonine at δ3,780 allowed the placement of an isoleucine rather than leucine in position 5, thereby placing the leucine at position 8. In addition, the TOCSY data, in conjunction with the DQFCOSY data, clearly showed the presence of a γ-methyl proline rather than a piperidine carboxylic acid, or another isomeric methyl proline moiety. Correlations of the y-methylproline C-αH signal at δ4,050 ppm could be seen in the D-methylene with signals at δ2,019 ppm and δ0.38 ppm. A correlation to the methyl signal at δ2,019 ppm and δ0.38 ppm. A correlation to the methyl signal at δ0.872 ppm allows the placement of a methyl at the y-position due to the consequent correlation of the δ methylene protons at δ3.14 ppm, and δ3.83 ppm.

The molecule is closely related to the peptaibol class of compounds (most particularly, Zervamicin II-3) so named because of the presence of 2-aminoisobutyric acid residues plus alcohol analogs of amino acids on the C-terminus such a phenylalinol.

Example 12

Circular Dichroic Spectropolarimetry

A. Circular Dichroic Sample Preparation and Quantitation

All samples were prepared by dissolving weighed amounts (2–4 mg) of freshly vacuum-dried peptides directly in 2 mM aqueous phosphate buffer (nominal pH 9) to produce stock solutions with nominal concentrations of ⁻400–600 μg/mL. The concentrations of the stock solutions were determined by UV assuming the following absorptivities: Trp $\epsilon_{282}$=5011.9. The UV measurements were made in the non-denaturing medium used for the stock solution, rather than in 6 M guanidinium HCl, as suggested in the literature. UV spectra were recorded with a Hewlett Packard 8452A diode array spectrophotometer. Buffers were freshly prepared using MILLI-Q System (Millipore Corp., Bedford, Mass.) high purity water. The pH was measured using a Corning pH meter that was regularly calibrated with buffer standards (pH 4 and 7). All solvents were spectrophotmetry grade or better.

B. Circular Dichroic Spectropolarimetry

CD Spectra were recorded at normal operating temperature (⁻25° C.) using a JASCO model J720 spectropolarimeter, which had stabilized for at least 30 minutes with a nitrogen flow rate of 10 L/min. The wavelength and degree ellipticity scales were frequently calibrated using the d-10-camphorsulfonic acid (CSA) sample provided by the manufacturer. For the far UV range, we assume that the CSA minimum corresponds to $\theta_{192.5}$=−15, 600. All subsequent CD spectral values for peptides are expressed in units of residue molar ellipticity (deg cm²/residue-dmol) based on a residue count corresponding to the number of amide carbonyls in the backbone. Typical spectral accumulation parameters were: time constant, 0.25 s; scan rate, 100 nm/minute with a 0.2 nm step resolution over the range 178–270 nm; with 16 scans averaged for each spectrum. The accumulated average spectra were trimmed at a dynode voltage of 650 prior to baseline subtraction and smoothing using the reverse Fourier transform procedure in the JASCO software. Final peptide concentrations of 12–110 μM in the CD quartz cells (typically of 0.5 mm path length) were obtained by quantitative serial dilution of the stock solutions. The aqueous buffers used for the CD solutions were 10 mM phosphate (pH 3.2, 4.0, 4.6, 6.0, 7.5 or 8.0). Between samples the cells were rinsed, in sequence, with distilled water, methanol, distilled water, methanol, and finally acetone, before drying in a purified nitrogen stream. The method of serial dilution deserves some comment. In order to avoid previously noted evaporation and mixing volume problems associated with fluoroalcohol containing media, a 300–800 μl portion of a premixed ratio of aqueous buffer and fluoroalcohol was added to a 40–120 μl portion of aqueous stock solution and the resulting solution was immediately transferred to the CD cuvette for measurement within 5 minutes of mixing. All volume measurements and transfers were accomplished with high precision microliter syringes.

| Raw Curve Shape Data: Natural Product 2807 | | | | | | | |
|---|---|---|---|---|---|---|---|
| pH or Solvent | $\theta_{222}$ | nm | $\theta_{min}$ | nm | $\theta_{max}$ | nm | $\theta_{other}$ | nm |
| 3.0 | −3561 | 229.2 | −5360 | 208.2 | 14290 | 196.0 | | |
| 9.1. | −2028 | 236.0 | −3420 | 207.0 | 8760 | 196.4 | 630 | 218.4 |
| 4.4 | −1753 | 231.6 | −3635 | 206.4 | 9325 | 196.4 | 475 | 218.8 |
| 6.0 | −1939 | 233.0 | −3910 | 206.6 | 9380 | 196.4 | 650 | 219.0 |
| 11.0 | −2007 | 234.2 | −3860 | 206.4 | 10000 | 196.4 | 350 | 219.0 |
| 25% TFE | −5951 | 228.4 | −12370 | 207.2 | 28930 | 194.2 | | |
| 296 mM | −3105 | 229.2 | −5610 | 207.8 | | | | |
| 98.7 mM | −1730 | 232.0 | −3650 | 206.8 | 9150 | 196.6 | 565 | 218.0 |
| 59.2 mM | −1740 | 233.0 | −3870 | 207.0 | 8490 | 196.4 | 585 | 218.0 |
| 29.6 mM | −1343 | 234.2 | −2810 | 206.4 | 7010 | 196.4 | 675 | 218.0 |
| 14.8 mM | −1584 | 234.8 | −2730 | 207.0 | 6385 | 196.8 | 450 | 216.8 |
| 50% methanol | −2147 | 229.6 | −3900 | 207.4 | | | | |
| 50% glycol | −1616 | 230.2 | −3005 | 207.8 | | | | |
| 50% CH₃CN | −2141 | 229.2 | −4220 | 207.8 | 10590 | 195.2 | | |
| 10% glycol | −2232 | 231.0 | −4520 | 207.0 | 12275 | 196.4 | −300 | 217.6 |
| SDS 22:1 | −9081 | 222.8 | −11285 | 208.4 | 30950 | 195.4 | | |
| 10% TFE | −3977 | 229.6 | −7220 | 207.2 | 19225 | 195.4 | | |
| 60% TFE | −4578 | 228.0 | −9260 | 206.8 | 24525 | 194.6 | | |

Example 13

The Effect of calcitonin Mimetic on Bone Loss

The ability of calcitonin mimetics to prevent osteopenia induced by estrogen deficiency can be evaluated in the ovariectomized mouse model. Twenty-four female Swiss-Webster mice (8 weeks old) receive either an ovariectomy or sham surgery prior to the initiation of a 4 week treatment protocol. For the ovariectomy, a flank incision through the skin, muscle and abdominal peritoneum is made on each side, and the ovaries are located, dissected free of adherent fat and connective tissue, and excised. In the sham procedure the ovaries are exteriorized and replaced. In all animals the peritoneum and muscle are sutured together, and the skin incisions are closed with wound clips.

The calcitonin mimetic is dissolved in a minimal amount of dimethylsulfoxide and diluted in oil vehicle to a concentration of 50 µg/100 µL. The mice are treated daily for 4 weeks with a subcutaneous injection of calcitonin mimetic or oil vehicle according to the following outline: Sham/oil vehicle (SV); OVX/oil vehicle; OVX/50 µg calcitonin mimetic. There are 8 animals in each group.

At the conclusion of the 4-week calcitonin mimetic treatment, the mice are anesthetized with ether and sacrificed by cervical dislocation. Immediately after sacrifice, the femurs are removed and fixed in 70% ethyl alcohol (EtOH) and dehydrated undecalcified in a series of increasing alcohol concentrations using a VIP 2000 Automatic Tissue Processor (Miles Scientific, Elkart, Ind.): 80 and 95% EtOH followed by three changes in 100% EtOH. After the final 100% EtOH the femurs are cleared in two changes of xylene and then embedded in methylmethacrylate plastic according to previously described methods (Bain et al., *Stain Technology* 65:159–63, 1990). Five micrometer frontal sections of the distal metaphyses are cut on a Reichert-Jung 2050 rotary microtome equipped with a tungsten-carbide knife. The 5 µm sections are mounted on glass slides and stained with Goldner's trichrome stain or stained for tartrate-resistant acid phosphatase activity, or unstained for evaluation of fluroochrome labels.

Histomorphometric measurements of the distal metaphyses are determined using the Bioquant Bone Morphometry Program (Biometrics, Inc., Nashville, Tenn.) interfaced via a camera lucida with an Olympus BH-2 light/epifluorescent microscope (Scientific Instruments, Inc., Redmond, Wash.). Morphometric measurements of cancellous bone volume (BV/TV) as well as other bone parameters are performed in the tissue space greater than 0.25 mm from the growth plate-metaphyseal junction to exclude primary spongiosa.

Example 14

Caco-3 Epithelial Transport

Caco-2 cells are human colon adenocarcinoma cells which, when grown in culture, differentiate to form monolayers that look and behave much like human small intestinal epithelium (Hidalog et al., *Gastroenterology* 96:736–49, 1989; Hilgers et al., *Pharm. Res.* 7:902–10, 1990). The Caco-2 monolayer system has been used as an in vitro model to study peptide transport across the intestinal mucosa (Conradi et al., *Pharm. Res.* 8:1453–60, 1991; Conradi et al., *Pharm. Res.* 9:435–39, 1992) and has shown a good correlation with intestinal absorption of peptides in rat (Conradi et al., *Pharm. Res.* 10:1790–92, 1993) and oral absorption of drugs in humans (Artursson and Karlsson, *Biochem. Biophys. Res. Commun.* 175:880–85, 1991).

To determine permeability and transport across the intestinal membrane, a CaCo-2 monolayer can be grown on a microporous membrane (6.5 mm collagen-coated polyethylene terephthalate (PET) (Becton Dickinson, Sparks, Md.), 6.5 mm Transwell collagen-coated PTFE or Transwell polycarbonate membranes (Costar, Pleasanton, Calif.)). All membrane inserts are designed to fit into 24-well plates. Caco-2 cells (ATCC HTB-37) are propagated in Minimum Essential Medium (MEM) (GIBCO BRL, Gaithersberg, Md.) supplemented with 1% L-glutamine, 20% FBS and 1% MEM nonessential amino acid solution (GIBCO BRL). Filters are seeded at $4 \times 10^5$ cells/ml and grown for 6–25 days at 37° C., 5% $CO_2$. Monolayers are then placed in Hank's Balanced Salt Solution (GIBCO BRL) where 0.5 µCi/ml 1 µM transport chemical or $^3$H-synthetic mimetic (at various concentrations) are added to either the apical or basal side of the monolayer. Transport chemicals can include $^3$H-PEG, $^3$H-mannitol or $^{14}$C taucholic acid. Medium in the unlabeled chamber is changed every 15 minutes and analyzed using a LS6500 Multi Purpose Scintillation Counter (Beckman). PEG has been shown to be relatively impermeable to Caco-2 monolayers, while mannitol more readily diffuses across the monolayer and designates a minimum permeability for orally available compounds. Taucholic acid has been shown to be directionally transported in an apical to basal direction.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

---

What is claimed is:
1. A compound selected from the group consisting of:
   Acetyl-Trp-Xaa$_1$-Gln-Xaa$_2$-Ile-Thr-Xaa$_3$-Leu-Xaa$_4$-pro-Gln-Xaa$_5$-Pro-Xaa$_6$-Xaa$_7$-Phe-Gly-COOH (SEQ ID NO. 1);

Acetyl-Trp-Xaa$_1$-Gln-Xaa$_2$-Ile-Thr-Xaa$_3$-Leu-Xaa$_4$-Pro-Gln-XaaS-Pro-Xaa$_6$-Xaa$_7$-Phe-COOH (SEQ ID NO.2); and pharmaceutically acceptable salts thereof, wherein Acetyl is $CH_3CO$—, Xaa$_1$ is isovaline, Xaa$_{2,3,4,5,}$ and $_6$ are 2-aminoisobutyric acid and Xaa$_7$ is 4-methyl proline.

2. A pharmaceutical composition comprising a compound according to claim 1 in combination with a pharmaceutically acceptable carrier.

3. A method of inhibiting bone resorption comprising administering to a patient in need of such inhibition a pharmaceutical composition of claim 2.

4. A method according to claim 3, wherein the patient is suffering from osteoporosis, Paget's disease or hyperparathyroidism.

5. A pharmaceutical composition according to claim 2, wherein said composition is formulated for oral administration.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="Xaa1 is D- or L-Arg, D- or
        L-Lys, D- or L-Orn, or absent with the proviso that
        whatever amino acid is the N terminal amino acid is
        substituted with hemisuccinimide, or R1-CO-, wherein
        R1 is selected from the group consisting of: hydrogen;
        linear or branched alkyl, alkenyl, or alkynyl of not
        more than 32 carbon atoms; unsubstituted mono- or poly-
        cycloalkyl or mono- or poly-cycloalkylmethyl of not more
        than 20 carbon atoms, not more than 4 rings, each ring
        having 5-6 carbon atoms; unsubstituted mono- or poly-aryl
        or mono- or poly-arylmethyl of not more than 20 carbon
        atoms, not more than 4 rings, each ring having 5-6
        carbon atoms; and unsubstituted mono- or poly-heteroaryl
        or mono- or poly-heteroarylmethyl of not more than 20
        atoms, not more than 4 rings, each ring having 5-6 ring
        atoms and not more than 4 heteroatoms, in which the
        heteroatoms are selected from the group consisting of: N,
        O, and S."

( i x ) FEATURE:
    ( A ) NAME/KEY: Modified-site
    ( B ) LOCATION: 2
    ( D ) OTHER INFORMATION: /note="Xaa2 is a D- or L- aromatic
        amino acid, an unnatural aromatic amino acid, Cys, Pen,
        or absent, with the proviso that when Xaa2 is Cys or Pen,
        Xaa8 is Cys or Pen."

( i x ) FEATURE:
    ( A ) NAME/KEY: Modified-site
    ( B ) LOCATION: 3
    ( D ) OTHER INFORMATION: /note="Xaa3 is an a-alkylated a amino
        acid, a b- branched amino acid, or absent, with the
        proviso that when Xaa16 is 4-methyl proline, Xaa3 is
        Aib."

( i x ) FEATURE:
    ( A ) NAME/KEY: Modified-site
    ( B ) LOCATION: 4
    ( D ) OTHER INFORMATION: /note="Xaa4 is Gln, Asn, His, or a
        substituted amide (R2-NH-Z), wherein Z is an a- or g-acyl
        radical of Asn or Gln, and R2 is selected from a group
        consisting of: polyethylene glycol (PEG); linear or
        branched alkyl, alkenyl, or alkynyl of not more than 32
        carbon atoms; unsubstituted mono- or poly-cycloalkyl or
        mono- or poly-cycloalkylmethyl of not more than 20 carbon
        atoms, not more than 4 rings, each ring having 5-6 carbon
        atoms; unsubstituted mono- or poly-aryl or mono- or poly-
        arylmethyl of not more than 20 carbon atoms, not more
        than 4 rings, each ring having 5-6 carbon atoms; and
        unsubstituted mono- or poly-heteroaryl or mono- or
        poly- heteroarylmethyl of not more than 20 atoms, not
        more than 4 rings, each ring having 5-6 ring atoms,
        and not more than 4 heteroatoms, wherein the
        heteroatoms are selected from the group consisting
        of: N, O, and S."

( i x ) FEATURE:
    ( A ) NAME/KEY: Modified-site
    ( B ) LOCATION: 5
    ( D ) OTHER INFORMATION: /note="Xaa5 is an a-alkylated a amino
        acid, or a D- amino acid."

( i x ) FEATURE:
    ( A ) NAME/KEY: Modified-site
    ( B ) LOCATION: 6
    ( D ) OTHER INFORMATION: /note="Xaa6 is a b-branched amino
        acid, or an aliphatic amino acid."

( i x ) FEATURE:
    ( A ) NAME/KEY: Modified-site
    ( B ) LOCATION: 7
    ( D ) OTHER INFORMATION: /note="Xaa7 is a b-branched amino
        acid, an H- bond donor amino acid, or absent."

( i x ) FEATURE:
    ( A ) NAME/KEY: Modified-site (B) LOCATION: 8
(D) OTHER INFORMATION: /note="Xaa8 is an a-alkylated a
    amino acid, a D-amino acid, Pen, Cys, or absent, with
    the proviso that when Xaa8 is Cys or Pen, Xaa2 is Cys
    or Pen."

(ix) FEATURE:
  (A) NAME/KEY: Modified-site
  (B) LOCATION: 9
  (D) OTHER INFORMATION: /note="Xaa9 is a b-branched amino
      acid, an aliphatic amino acid, or absent."

(ix) FEATURE:
  (A) NAME/KEY: Modified-site
  (B) LOCATION: 10
  (D) OTHER INFORMATION: /note="Xaa10 is an a-alkylated a
      amino acid, a D-amino acid, or absent."

(ix) FEATURE:
  (A) NAME/KEY: Modified-site
  (B) LOCATION: 11
  (D) OTHER INFORMATION: /note="Xaa11 is Pro, pipecolic acid,
      thiazolidine carboxylic acid, 3- or 4-hydroxyproline,
      dehydroproline, 3- or 4-methylproline, 3,3-
      dimethylproline, N-alkyl alanine, or absent."

(ix) FEATURE:
  (A) NAME/KEY: Modified-site
  (B) LOCATION: 12
  (D) OTHER INFORMATION: /note="Xaa12 is Gln, Asn, Arg, His,
      absent, or a substituted amide (R2-NH-Z), wherein Z is
      an a- or g- acyl radical of Asn or Gln, and R2 is
      selected from a group consisting of: polyethylene
      glycol (PEG); linear or branched alkyl, alkenyl, or
      alkynyl of not more than 32 carbon atoms; unsubstituted
      mono- or poly-cycloalkyl or mono- or poly-
      cycloalkylmethyl of not more than 20 carbon atoms, not
      more than 4 rings, each ring having 5-6 carbon atoms;
      unsubstituted mono- or poly-aryl or mono- or poly-
      arylmethyl of not more than 20 carbon atoms, not more
      than 4 rings, each ring having 5-6 carbon atoms; and
      unsubstituted mono- or poly-heteroaryl or mono- or poly-
      heteroarylmethyl of not more than 20 atoms, not more than
      4 rings, each ring having 5-6 ring atoms, and not more
      than 4 heteroatoms, wherein the heteroatoms are selected
      from the group consisting of: N, O, and S."

(ix) FEATURE:
  (A) NAME/KEY: Modified-site
  (B) LOCATION: 13
  (D) OTHER INFORMATION: /note="Xaa13 is an a-alkylated a
      amino acid; a D-amino acid; or absent."

(ix) FEATURE:
  (A) NAME/KEY: Modified-site
  (B) LOCATION: 14
  (D) OTHER INFORMATION: /note="Xaa14 is Pro, pipecolic acid,
      thiazolidine carboxylic acid, 3- or 4-hydroxyproline,
      3- or 4- methylproline, dehydroproline, 3,3-
      dimethylproline, N-alkyl alanine, or absent."

(ix) FEATURE:
  (A) NAME/KEY: Modified-site
  (B) LOCATION: 15
  (D) OTHER INFORMATION: /note="Xaa15 is an a-alkylated
      a-amino acid, a D-amino acid; or absent."

(ix) FEATURE:
  (A) NAME/KEY: Modified-site
  (B) LOCATION: 16
  (D) OTHER INFORMATION: /note="Xaa16 is Pro, pipecolic acid,
      thiazolidine carboxylic acid, 3- or 4-hydroxyproline, 3-
      or 4- methylproline, dehydroproline, 3,3-dimethylproline,
      N-alkyl alanine, or absent."

(ix) FEATURE:
  (A) NAME/KEY: Modified-site
  (B) LOCATION: 17
  (D) OTHER INFORMATION: /note="Xaa17 is a D- or L-aromatic
      amino acid; an unnatural aromatic amino acid; or absent."

(ix) FEATURE:
  (A) NAME/KEY: Modified-site
  (B) LOCATION: 18
  (D) OTHER INFORMATION: /note="Xaa18 is Asp, Glu or absent,
    with the proviso that whatever amino acid occupies the C
    terminus the following C terminal substitutions are
    possible: hemisuccinimide, R3-Z, wherein, when Z is an
    aminoacyl radical of Xaa17, R3 is: OH, NH2, NH-PEG, or
    NHCH2(CH2)n- R4, wherein n=32 and R4 is hydrogen or an a
    amino acid; or wherein, when Z is an a-aminoalkyl
    radical of Xaa17, R3 is: COOH, CONH2, CONH-PEG, or
    CONHCH2(CH2)n-R4, wherein n=32 and R4 is hydrogen or an
    a amino acid; or a substituted amide (R2-NH-Z), wherein
    Z is an a- or g-acyl radical of Xaa18, and R2 is
    selected from a group consisting of: polyethylene glycol
    (PEG); linear or branched alkyl, alkenyl, or alkynyl of
    not more than 32 carbon atoms; unsubstituted mono- or
    poly- cycloalkyl or mono- or poly-cycloalkylmethyl of not
    more than 20 carbon atoms, not more than 4 rings, each
    ring having 5-6 carbon atoms; unsubstituted mono- or
    poly-aryl or mono- or poly-arylmethyl of not more than
    20 carbon atoms, not more than 4 rings, each ring having
    5-6 carbon atoms; and unsubstituted mono- or poly-
    heteroaryl or mono- or poly-heteroarylmethyl of not more
    than 20 atoms, not more than 4 rings, each ring having
    5-6 ring atoms, and not more than 4 heteroatoms, wherein
    the heteroatoms are selected from the group consisting
    of: N, O, and S."

(xi) SEQUENCE DESCRIPTION: SEQ ID NO:1:

Xaa Xaa Xaa Xaa Xaa Xaa Xaa Xaa Xaa Xaa Xaa Xaa Xaa Xaa Xaa Xaa
1               5                   10                  15

Xaa Xaa (2) INFORMATION FOR SEQ ID NO:2:

(i) SEQUENCE CHARACTERISTICS:
    (A) LENGTH: 16 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Modified-site
    (B) LOCATION: 1
    (D) OTHER INFORMATION: /note="N-terminal acetyl group (CH3)."

(ix) FEATURE:
    (A) NAME/KEY: Modified-site
    (B) LOCATION: 2
    (D) OTHER INFORMATION: /note="All Xaa are Aib"

(ix) FEATURE:
    (A) NAME/KEY: Modified-site
    (B) LOCATION: 16
    (D) OTHER INFORMATION: /note="C terminal has -COOH group."

(xi) SEQUENCE DESCRIPTION: SEQ ID NO:2:

Trp Xaa Gln Xaa Ile Thr Xaa Leu Xaa Pro Gln Xaa Pro Xaa Pro Phe
1               5                   10                  15